United States Patent [19]
Thompson et al.

[11] Patent Number: 5,154,081
[45] Date of Patent: Oct. 13, 1992

[54] MEANS AND METHOD FOR ULTRASONIC MEASUREMENT OF MATERIAL PROPERTIES

[75] Inventors: Robert B. Thompson; Samuel J. Wormley, both of Ames, Iowa; George A. Alers, Albuquerque, N. Mex.

[73] Assignee: Iowa State University Research Foundation, Inc., Ames, Iowa

[21] Appl. No.: 647,484

[22] Filed: Jan. 28, 1991

Related U.S. Application Data

[62] Division of Ser. No. 383,760, Jul. 21, 1989, abandoned.

[51] Int. Cl.$^5$ ............................................ G01N 29/18
[52] U.S. Cl. ........................................... 73/597; 73/643
[58] Field of Search ........................... 73/643, 597, 641

[56] References Cited

U.S. PATENT DOCUMENTS

| | | | |
|---|---|---|---|
| 3,720,098 | 3/1973 | Dixon . | |
| 4,184,374 | 1/1980 | Thompson et al. | 73/643 |
| 4,218,924 | 8/1980 | Fortunko et al. | 73/643 |
| 4,348,903 | 9/1982 | Sato et al. | 73/643 |
| 4,399,702 | 8/1983 | Suzuki . | |
| 4,432,234 | 2/1984 | Jones | 73/597 |
| 4,522,071 | 6/1985 | Thompson | 73/643 |
| 4,599,563 | 7/1986 | Tiitto et al. . | |
| 4,790,188 | 12/1988 | Bussiere et al. | 73/597 |
| 4,899,589 | 2/1990 | Thompson et al. | 73/597 |

OTHER PUBLICATIONS

R. B. Thompson et al., "Angular dependence of ultrasonic wave propagation in a stressed orthorhombic continuum: Theory and application to the measurement of stress and texture", J. Acoust. Soc. Am. 80(3), Sep. 1986, pp. 921–931.

R. B. Thompson, et al., "Inference of Stress and Texture from the Angular Dependence of Ultrasonic Plate Mode Velocities," Non-Destractive Evaluation of Microstructure for Process Control, H. N. G. Wodley, Ed (ASM, Metal Pack, Ohio, 1985), pp. 73–79.

Primary Examiner—John E. Chapman
Attorney, Agent, or Firm—Zarley, McKee, Thomte, Voorhees & Sease

[57] ABSTRACT

The system for field measurement of texture, stress and related material properties such as formability parameters using ultrasonic velocity measurements through crystalline plate or sheet. Electromagnetic acoustic transducers are utlized to generate, transmit, and receive ultrasonic bursts through the plate at different angular orientations with respect to the plane of the plate. Two of the transducers are driven in series when generating the ultrasonic bursts. Time measurements between transmission and reception of the bursts are precisely derived and converted into velocities. Information regarding stress, texture, and other related material properties such as formability parameters can be derived from these velocity measurements. The system is adjustable to be used for both ferrous and nonferrous crystalline plate. Alteration of the types of ultrasonic waves utilized, and the methods of generating the waves allows different properties such as texture and stress to be derived.

25 Claims, 5 Drawing Sheets

RECEIVED WAVEFORMS FROM $T_1$ AND $T_2$

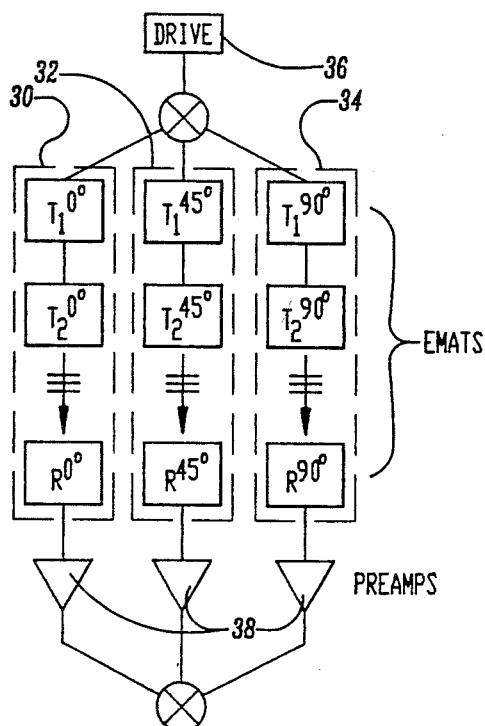
Fig.4
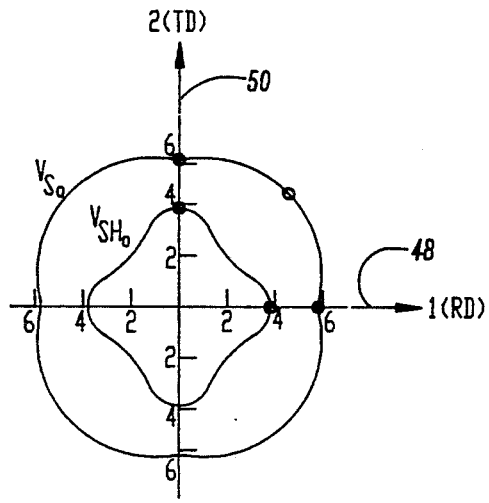
Fig.5
SH₀ WAVES IN TEXTURED MEDIA
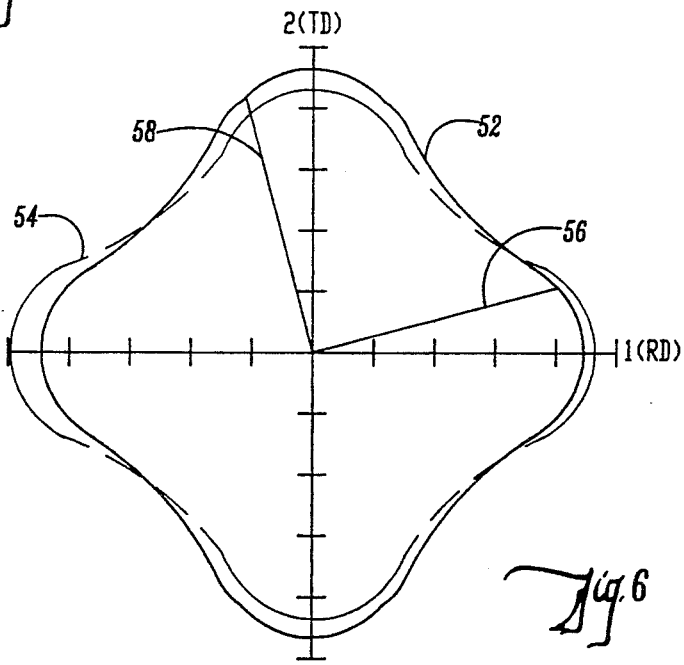
Fig.6
|  | TEXTURE | STRESS |  |
|---|---|---|---|
| FERROUS | 0,45,90 | 0,90 | PULSED MAGNETS |
| NON-FERROUS | 0,45,90 | 0,90 | PERMANENT MAGNETS |
|  | S₀ | SH₀ |  |
Fig.7

EQUIVALENT CIRCUIT
LIFTOFF INTRODUCES
PHASE SHIFT

MEANDER-COIL EMAT WITH BIAS FIELD CONFIGURED FOR
GENERATING HORIZONTALLY POLARIZED SHEAR WAVES $S_0$ (LAMB WAVE) EMAT ARRAY

MEANS AND METHOD FOR ULTRASONIC MEASUREMENT OF MATERIAL PROPERTIES

This is a divisional of copending application Ser. No. 07/383,760 filed on Jul. 21, 1989 abandoned.

BACKGROUND OF THE INVENTION

1. Field of the Invention

The present invention relates to the use of ultrasound in nondestructive evaluation, and particularly to the use of ultrasound in a field instrument for measuring texture, stress, and related material properties to infer properties relating to formability in sheet or plate having crystalline structure.

2. Problems in the Art

Nondestructive evaluation (NDE) is of great and increasing importance in present day technological environments. Prominent NDE systems utilizing ultrasound, x-ray diffraction and magnetic evaluation, among others, enable analysis of a wide variety of materials relatively efficiently and economically. Obviously, NDE has the primary advantage of avoiding destructively sampling the material being analyzed.

The advantages of NDE are widely known. Developments continue with regard to all areas of NDE.

Ultrasonic methods of NDE have particular advantages over other types of NDE under recent circumstances. Recent advances have broadened the applicability of ultrasonic NDE and the accuracy of ultrasonic NDE.

While the advantages and advances with regard to ultrasonic NDE have been realized in laboratory settings, there is still a real need in the art for methods and instruments which can be utilized directly in the manufacturing processes and environments for the materials being analyzed, and to be able to be used in a variety of locations and situations for evaluating parts and materials during their life span.

There is a very real need for an accurate, fast, and reliable system to measure and analyze materials nondestructively, in process or at an easily accessible location, that is, in the field.

For example, in the manufacture of metal sheet or plate, the manufacturing process produces a texture (or preferred grain orientation) in the sheet or plate because of the crystalline structure of metal. This texture, as is well known in the art, affects the material properties and characteristics of the sheet or plate. It is therefore valuable first to know what type of texture the sheet or plate has, and second, to be able to use that information to infer properties relating to the formability of the plate or sheet.

By way of another example, it is valuable and indeed critical to be able to analyze the integrity of in-use parts and materials such as airplane wings. Detection of stresses within the wing can enable the wing to be removed or repaired before failure.

While there are many different methods and apparatus which are currently being used or have attempted to be used to meet these needs, none has successfully achieved all of these needs in one field instrument and method. Furthermore, in ultrasonic NDE, there are many areas where accuracy and reliability of the ultrasonic investigation, and the results derived from it, are significant.

There is therefore a real need in the art for a field instrument for ultrasonic measurement of material properties in plate or sheet of crystalline structure which is nondestructive, is adaptable to on-line or in process environments, is easily movable and usable at a variety of locations, is easy to operate, accurate, and reliable, and can be used to measure a variety of material properties for a variety of materials.

In real world situations this means that such a means and method must be usable in environments of wide ranging temperatures, such as in on-line manufacturing of metal plate where very high temperatures exist. It also must be of a size which can be practically portable, both as to the ultrasonic transducers and the components operating the transducers and deriving results from the transducers. Moreover, it must be easily operable and durable.

It is also important to understand that a need exists for such an instrument which can accurately measure as many material properties as possible, for as many different types of materials as possible. There is a need, therefore, for investigative transducers which are adaptable to a variety of situations and materials, a need for the ability to measure a variety of material properties such as texture and stress, and a need to analyze a variety of types of materials, for example, ferrous materials and nonferrous materials.

To enable such flexibility, the control and processing equipment must be adaptable to that variety, and also must solve or compensate for problems and potential error influences that can occur.

For example, ultrasonic transducers can experience problems with lift-off in settings where there is not the ability for precise laboratory controls. Compensation and control of any effect to the processing of the ultrasonic signals must be compensated for. Additionally, the instrument must be flexible to allow interchangeability of components for various situations. Ferrous materials, for example, may require different types of transducers than nonferrous materials.

Finally, the instrument must be accurate to within acceptable margins of error. Processing of the signals obtained by the transducers must therefore be accomplished to meet this error margin.

It is therefore a principal object of the present invention to provide a field instrument means and method for ultrasonic measurement of texture, stress and related material properties to infer properties relating to formability in crystalline sheet or plate which improves over or solves the problems and deficiencies in the art.

A further object of the present invention is to provide a means and method as above described which allows efficient and accurate implementation of ultrasonic nondestructive evaluation.

A further object of the present invention is to provide a means and method as above described which allows nondestructive measurement of a variety of material properties including texture and stress accurately and reliably.

Another object of the present invention is to provide a means and method as above described which effectively and flexibly allows nondestructive ultrasonic evaluation of a variety of materials in process or on location.

Another object of the present invention is to provide a means and method as above described which is flexible in its adaptability and adjustability for different materials and different material properties.

A still further object of the present invention is to provide a means and method as above described which can nondestructively evaluate materials which are either stationary or moving at unknown speeds.

Another object of the present invention is to provide a means and method as above described which can facilitate process control of materials or monitor residual or applied stress during the life cycle of the material.

Another object of the present invention is to provide a means and method as above described which can function accurately and reliably in a variety of different environments and locations.

A still further object of the present invention is to provide a means and method as above described which can quickly process ultrasonic transducer signals and produce accurate and reliable results regarding material properties such as formability parameters of the material investigated.

These and other objects, features, and advantages of the present invention will become more apparent with reference to the accompanying specification and claims.

SUMMARY OF THE INVENTION

The present invention relates to a field instrument means and method for ultrasonic measurement of texture, stress, and related material properties in crystalline sheet or plate to derive formibility parameters. It allows the advantages achieved by nondestructive ultrasonic evaluation in non-laboratory settings. It also allows a unitary, portable system to be effectively and accurately utilized to evaluate a number of different metal sheet or plate materials in a number of different locations or environments.

The invention utilizes the transmission of ultrasonic energy into the specimen being investigated, and derives the velocity of the ultrasonic energy through the specimen. Such ultrasonic measurements are made in two or more angular orientations with regard to the plane of the plate or sheet specimen. The received signals are then processed to derive material properties of the specimens such as texture and stress.

The present invention is generally limited to crystalline plate or sheet of less than $\frac{1}{4}$ inch in thickness. The plate or sheet can be ferrous or nonferrous. The invention is adaptable to operate with different transducers and in different ways to facilitate its use in different environments, for different materials, and for different material property measurements.

The invention consists of an interchangeable array of ultrasonic transducers which are connected to a portable housing for the processing components. The transducers are electromagnetic acoustic transducers (EMATs), which do not require a couplant to allow efficient transmission and reception of ultrasonic energy in and out of the specimen being analyzed. The transducers are also configured so that for each measurement direction, a set of two transmitting transducers are associated with one receiving transducer. The two transmitting transducers are operated in series to compensate for differential phase shifts due to lift-off of the transducers with respect to the material.

Different types of transducers are utilized for ferrous materials as compared to nonferrous materials. Additionally, different types of transducers are utilized for measuring texture as compared to measuring stress.

The present invention also includes signal processing which allows for the accurate derivation of ultrasonic wave speeds, compensates for any possible dispersion, and improves reliability of the results.

The present invention utilizes means and methods in a variety of combinations to achieve the objects of the invention.

BRIEF DESCRIPTION OF THE DRAWINGS

FIG. 4 is a schematic of one generalized organization for the transducers and processing components according to the present invention.

FIG. 5 is a graphic representation depicting the angular dependence of texture on the velocities of ultrasonic energy (both Lamb and horizontally polarized shear waves) through a specimen.

FIG. 6 is a graphic depiction of the effect of stress on the velocities of ultrasonic energy through a specimen.

FIG. 7 is a matrix depicting the flexibility and applicability of the present invention for various specimens and for various material property measurements.

DETAILED DESCRIPTION OF THE PREFERRED EMBODIMENT

Figure 1:
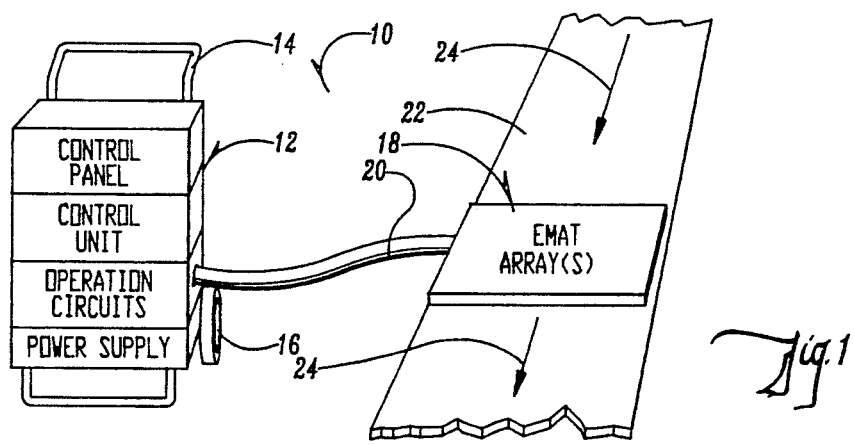
FIG. 1 is a schematic view of one embodiment of the invention.

To assist in an understanding of the invention, a preferred embodiment of the invention will be described in detail. This preferred embodiment does not, nor is it intended to, limit or restrict the invention. This description refers to the drawings. Reference numerals will be used in the drawings to refer to components and features. Like reference numerals will be used for like parts in all of the drawings unless otherwise indicated.

Ultrasonic nondestructive evaluation has been used in the art to analyze properties of different materials. In real world practice, however, there has not been developed a viable, accurate and reliable field instrument and technique which is applicable to many different types of metal plate or sheet materials and to different highly pertinent material properties. Such a system would be extremely valuable in industry to assist in controlling processing and manufacturing of materials, and in evaluating manufactured materials for potential breakdown or failure. The ability to do this on location economically and nondestructively is extremely important and beneficial.

By referring to FIG. 1, a field instrument 10 according to the present invention is schematically depicted. A housing 12 would contain various processing and control components such as control panel, control and processing units, operation circuits, and power supply. To enhance portability, the housing and its contents would be of a size sufficient to be transported relatively easily, and moved by handle 14 and wheels 16 to the location manually.

To gather ultrasonic information, a transducer head 18 containing the desired array of transducers for a particular application would be communicated to the components and housing 12 via cable 20. This flexibility would allow the transducer head 18 to be placed in an operative position to a material to be analyzed such as rolled metal plate 22 which is in-process, on-location at the manufacturing facility. Arrows 24 represent the rolling direction of metal plate 22, which is moving at an unknown speed past transducer head 18. Transducer head 18 contains electromagnetic acoustic transducers (EMATs) which do not require couplant between the transducers and plate 22, and which can be supported with respect to plate 22 in a fixed position by support means well known or easily adapted by those skilled in the art.

The nature of the EMAT transducers, transducer head 18, cable 20, housing 12 and its components; and indeed the entire field instrument 10, is such that it can operate in a variety of environments, including the rather hostile high temperature environment of a rolled metal plate manufacturing location, for example.

The remainder of the drawings are directed to specifics of the field instrument according to the invention which allow the invention to achieve its advantages and meet its stated objectives.

Figure 2:
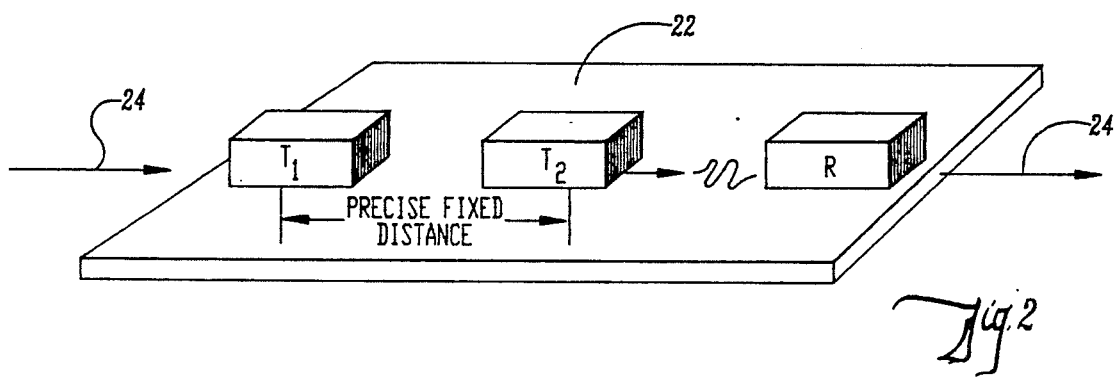
FIG. 2 is an isolated schematic view of an array of transmitting and receiving transducers according to the present invention.

FIG. 2 schematically depicts the basic configuration for the transmitting and receiving transducers used in the present invention. First and second transmitting transducers $T_1$ and $T_2$ are aligned along an axis with receiving transducer R. As shown, the distance between $T_1$ and $T_2$ is precisely fixed. The two transducers $T_1$ and $T_2$ are electrically connected in series.

In operation, this configuration along an axis is maintained with respect to the specimen under analysis such as plate 22. By any number of means known or obvious to those skilled in the art, the three transducers can be fixed in that configuration and still allowed to be positioned operatively adjacent to plate 22.

It is to be understood that this configuration of two transmitting transducers $T_1$ and $T_2$ with respect to receiving transducer R shall be referred to as one array of transducers. For purposes of the present invention, it is required that ultrasound be transmitted and measured not only along the rolling direction of the plate 22 (indicated by arrows 24), but also at offset angles from the rolling direction which will be identified as 0°. Therefore, each array of transducers is angularly adjustable between 0° to rolling direction, and 45° and 90° to rolling direction in the plane of plate 22. For an understanding of a similar relationship, and why measurements at these orientations are needed to measure material properties of texture in plate 22, reference is taken to co-pending U.S. patent application Ser. No. 197,763, entitled "Semiautomatic System For Ultrasonic Measurement of Texture", inventors R. Bruce Thompson and Samuel J. Wormley, filed May 23, 1988, and U.S. patent application Ser. No. 188,495, entitled "Method of Ultrasonic Measurement of Texture", by inventors R. Bruce Thompson, John F. Smith, Seung Seok Lee, and Yan Li, filed Apr. 29, 1988, both of which are incorporated by reference here.

Transducers $T_1$, $T_2$, and R are chosen to be EMAT transducers because they are couplant-free and can withstand the sometimes harsh and variable environments of in-process or on location use. They are also simple in construction and economical. It is further to be understood that each array of transducers can be angularly adjustable for various measurements, or alternatively, a plurality of fixed sets of transducers can be configured into the transducer head 18 at various measurement angles. This is the preferred way of constructing the transducer head 18 for the present invention (see FIG. 15 for example).

Figure 3:
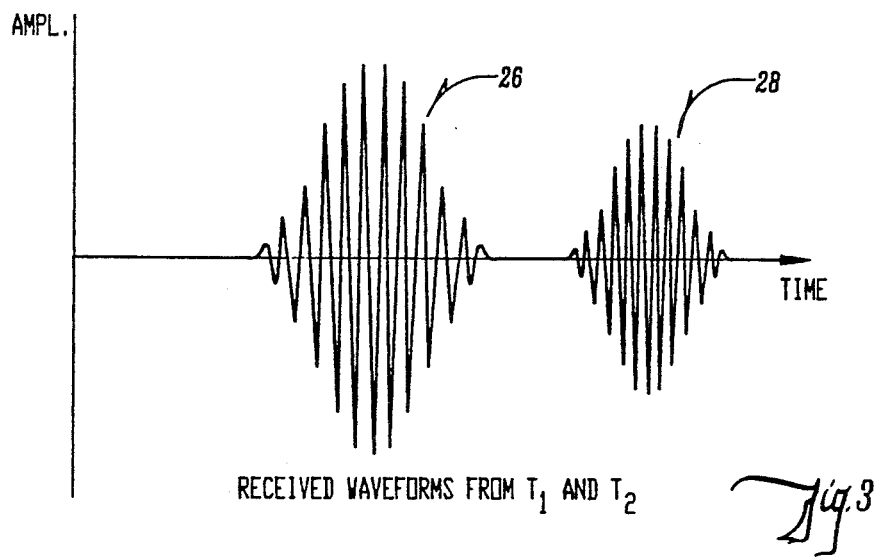
FIG. 3 is a graph of received wave forms from transducers $T_1$ and $T_2$ of FIG. 2.

FIG. 3 shows a graphic depiction of an exemplary received wave form from transducers $T_1$ and $T_2$ by a plot of amplitude of the signal versus time.

The present invention utilizes information derived from the anistropy of ultrasonic wave velocities at various angles with respect to the plate to obtain and derive various material properties of the plate. Transducer arrays are therefore utilized to time the ultrasonic waves between transmitters $T_1$ and $T_2$ and receiver R and convert those times to velocity, based on the known distance between the two transmitters $T_1$ and $T_2$. As set forth, for example, in the above referenced applications, when grains of a polycrystal are partially aligned, the ultrasonic wave speed will depend on the propagation direction due to the anisotropy of the single crystalelastic constant. This angular variation in terms of orientation distribution coefficients, $W_{lmn}$, defines texture of items such as metal plate. The ultrasonic velocities are also utilized in deriving formability parameters such as stress information regarding the specimen, such as will be described later.

A first feature of the preferred embodiment of the present invention is therefore the measurement of differential time between receipt of wave form 26 and wave form 28 for each array of transducer transmitters and receivers such as shown in FIG. 2. Velocity of the ultrasonic energy can then be computed from analysis of the reception time between wave forms 26 and 28 at receiver R.

FIG. 4 sets forth a simplified schematic of a general configuration for the operational portion of the field instrument 10. Three arrays of transducer sets 30, 32, and 34 would be positioned within transducer head 18, each array at a angular orientation to one another as indicated in FIG. 4; one array being at 0°, the second array at 45°, and the third array at 90°, all with relation to the array at 0°. Each array would utilize transducer transmitters $T_1$ and $T_2$ connected in series, operated at the same frequency, and aligned along an axis upon which a receiver R is also located. Each transducer pair $T_1$ and $T_2$ would be positioned at a precisely known distance from one another. A driving circuit 36, such as is known in the art would be multiplexed to each set of transducers $T_1$ and $T_2$.

The receiving transducers R would utilize preamps 38 to boost their signals, and be multiplexed to a receiver circuit 40 (main amplifier of the signals) which in turn would pass through a filter circuit 42, a scaling circuit 44 (a variable amplifier) and an analog-to-digital converter circuit 46, where those signals would be available to be communicated to a digital computer system or other control system.

The control system could therefore send instructions regarding how to drive the transmitting transducers, how to pull off the signals from the receiving transducers, and could process the signals.

FIG. 5 graphically depicts, to assist in an understanding of the invention, the angular dependence of ultrasonic wave speeds through a material with texture. Arrow 48 indicates rolling direction (otherwise considered 0°) whereas arrow 50 represents 90° from rolling direction. It can be seen that there is a four-fold symmetry with respect to both the extensional or Lamb waves (whose velocities are indicated by the solid line $V_{So}$, and horizontally polarized shear waves, represented by $V_{SHo}$.)

FIG. 5 therefore represents a kind of map of how velocities of both Lamb and shear ultrasonic waves vary in different angular orientations to the rolling direction of a specimen such as metal plate.

As described or referenced in the patent applications incorporated by reference herein, by obtaining the velocity of ultrasonic waves in the Lamb mode at 0°, 45° and 90°, the texture (preferred grain orientation) of the material can be derived.

A feature of the present invention is that by utilizing solely Lamb waves generated by transmitting transducers set up to generate Lamb waves, the appropriate information can be obtained to discern texture information regarding a material. This is not possible, however, using solely shear waves. Thus, the transducer head can contain Lamb-wave producing transducers and take measurements at 0°, 45° and 90° from the rolling direction to derive texture.

FIG. 6 illustrates graphically that stress can also be derived by the present invention, but utilizing horizontally polarized shear waves, not Lamb waves. Therefore, the transducer head of the instrument could be fitted with shear wave generating transducers to obtain appropriate measurements for deriving the stress information for the material. FIG. 6, similarly to FIG. 5 shows a graph of the velocity of ultrasound shear waves and its relationship angularly to the rolling direction of the material. The rolling direction again is along the horizontal axis to the right. Curve 52 depicts the angular dependence and velocity of ultrasonic shear waves through the texture of the material. Broken line 54 depicts the shifting of curve 52 upon application of stress to the specimen. It can be seen that the broken line expands along the horizontal axis, and contracts along the vertical axis.

Therefore, an explicit velocity shift is detected in the presence of stressed textured material.

It has been found by taking two orthogonal velocity measurements utilizing horizontally polarized shear waves (SH$_0$), represented by lines 56 and 58 in FIG. 6, stress can be derived for a material.

As an example, if the specimen was in a biaxial stress state in the plane of metal plate 22, principal stresses would be given values $\sigma_a$ and $\sigma_b$ inclined at an angle $\theta$ with respect to coordinates shown in FIG. 6. If the velocity of horizontally polarized ultrasonic shear waves propagating at an angle $\Omega$ with respect to the selected coordinates were taken and subtracted from the velocity measured at an angle $\theta + 90°$, it has been found that:

$$\rho V^2 = c_{66}(\sigma) = (\sigma_a + \sigma_b) - 2 + [(\sigma_a - \sigma_b) - 2]$$

$$\cos 2(\theta - \Omega) + [16\sqrt{35}/35 \times \pi^2 \ W_{440} + O(\sigma/c_{66})] \quad (1)(1 - 4\theta)$$

In equation 1, V is an average shear velocity. It can therefore be seen that measurement of the orthogonal velocities can be used to derive stress of the rolled metal plate.

The present invention can therefore be utilized to measure a variety of material properties. It has been shown that texture and stress can be measured with the same field instrument.

FIG. 7 depicts in matrix form characteristics of field instrument 10 and exemplifies its flexibility and use. As can be seen, instrument 10 can be used to measure the material properties of texture and stress; can be used to analyze both ferrous and nonferrous materials. The matrix in FIG. 7 shows that any combination of this information for these materials can be obtained by utilizing specific procedures. For example, to derive texture in ferrous materials, the transducers, in the preferred embodiment, must used pulsed magnets and Lamb waves where the measurements are taken at 0°, 45° and 90°. By comparison, stress in ferrous materials can be taken utilizing pulsed magnets, but only two measurements are needed, that being at 0° and 90°, and shear waves must be utilized.

Similarly, texture and stress can be derived in nonferrous materials at those same measurement directions with the same types of waves, but permanent magnets, in the preferred embodiment, are used.

To enable such application in the field, transducer head 18 is adaptable to have interchangeable transducer arrays according to which type of measurement, and for which type of material is being analyzed. Thus, if nonferrous materials are being analyzed, the transducers must utilize permanent magnets, and they must be configured between generating Lamb or shear waves according to whether texture or stress is being measured. For ferrous materials, pulsed magnets must be used and configured between shear and Lamb waves depending on whether texture or stress is being measured.

From equation 1 it is to be understood that the following equation is valid:

$$\frac{2\rho \vec{V}[V(\theta) - V(\theta + 90°)]}{\vec{V}} = (\sigma_a - \sigma_b) \quad (2)$$

Where $\vec{V}$ an average shear velocity. It is to be understood that this means that the velocity difference $[V(\theta) - V(\theta + 90°)]$ will be maximized when the ultrasonic propagation directions are aligned with the principal stress axes. It also reveals that the magnitude of this difference, along with the density and mean velocity can be used to predict the principal stress difference. It is particularly noteworthy that no acoustoelastic constants or other nonlinear properties of the material are needed for the stress prediction, which distinguishes this approach from other ultrasonic stress measurement techniques. The nonlinear material characteristics have been suppressed by the process of taking the velocity difference.

Figure 8:
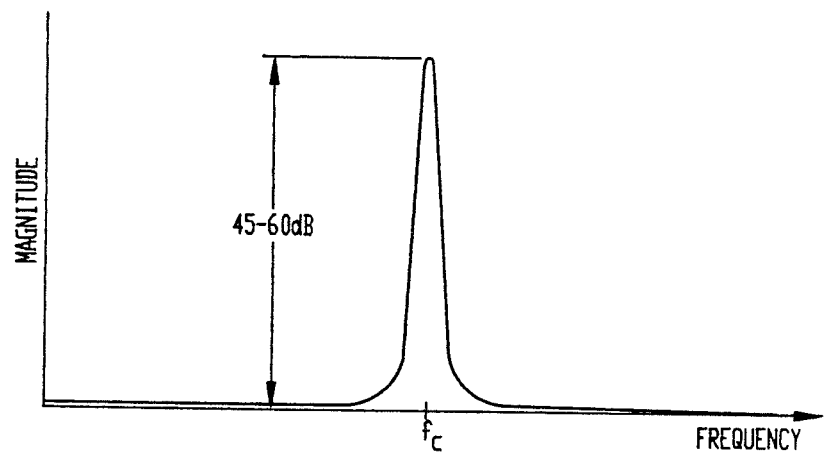
FIG. 8 is a graph showing a general depiction of magnitude versus frequency for a transducer according to the present invention.
Figure 9:
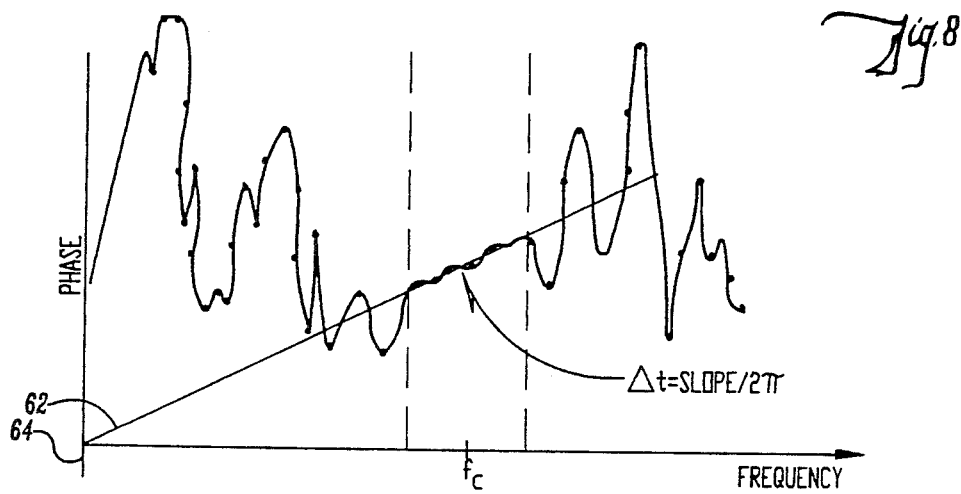
FIG. 9 is a graph of phase versus frequency showing the zone of operation for a transducer according to the present invention.

Another feature of the present invention is illustrated in FIGS. 8 and 9. A problem arises in utilizing the differential velocity measurements explained with regard to measuring the wave forms received from transducers T$_1$ and T$_2$ for each array. The difference in time of reception of these wave forms is considered as $\Delta t$. The preferred embodiment of the present invention needs to measure the time difference $\Delta t$ between bursts of wave forms to a precision of plus or minus 0.1 nanoseconds (nsec). However, the sampling rate is at 100 nsec.

By utilizing Fourier transform methodology, such as is known in the art, the time domain information regarding the bursts can be Fourier transformed into a frequency domain.

FIG. 8 shows a plot of magnitude versus frequency representative of the frequency band for the transducers according to the present invention. The value $f_c$ represents the center frequency for the transducers. The magnitude of the plot represents the signal to noise ratio of the transducer. In the present invention, this is normally within the 45–60 dB range.

FIG. 9 shows a plot of phase versus frequency with the center frequency of the transducers indicated along with the general band width for the transducers. According to the present invention, the signal outside of the band width of the transducer is contaminated with noise and other irrelevant components. However, the data points within the band range are clustered relatively closely to a line 62. The $\Delta t$ can be estimated by dividing the slope of line 62 by $2\pi$. By this method, an accurate estimation of $\Delta t$ can easily be derived. The slope is determined by linear regression, such as is well known in the art.

It has been found that considerable error may exist with regard to defining line 62 as it passes through the data points within the frequency band of the transducer. Therefore, another feature of the present invention is to designate that line 62 must pass through origin 64. This has been found to improve the degree of precision and reduce the error to within acceptable limits.

Additionally, because it is known that data points near the center frequence $f_c$ are more accurate than those near the edges of the band width, the data points near the center frequency can be assigned a higher weighting factor and improve the precision and reduce the error even more. Weighting at the center of the band width is desired because it is at this point where the signal-to-noise ratio is the best (see FIG. 8) The method for weighting data points based on the signal-to-noise ratio of each individual point.

Thus, instead of measuring the time between each corresponding point of the wave form of the two ultrasound bursts from $T_1$ and $T_2$ received at R, the Fourier transform — phase — slope determination of $\Delta t$ is easily and quickly accomplished with acceptable precision.

It has furthermore been found that utilizing EMAT transducers can result in potential error because of lift off of the transducers from the specimen being analyzed. To correct any potential error caused by lift off, the present invention utilizes the method of connecting and driving transducers $T_1$ and $T_2$ for each array in series. This assures that any change or shift in phase between the transducers is eliminated.

Figure 10:
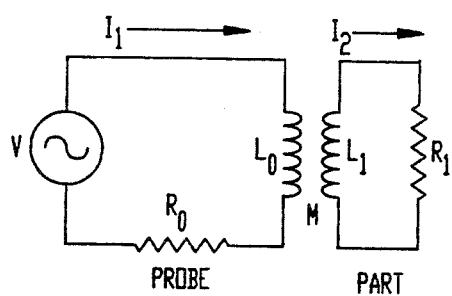
FIG. 10 is an electrical schematic showing equivalent electrical circuits for a transducer and the specimen which it is measuring.
Figure 11:
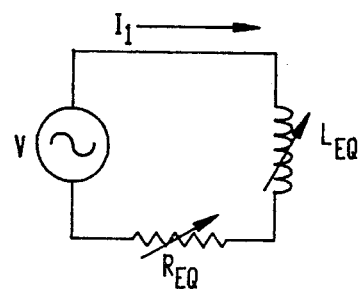
FIG. 11 is an electrical schematic of an equivalent electrical circuit combining the circuits of FIG. 10.
Figure 12:
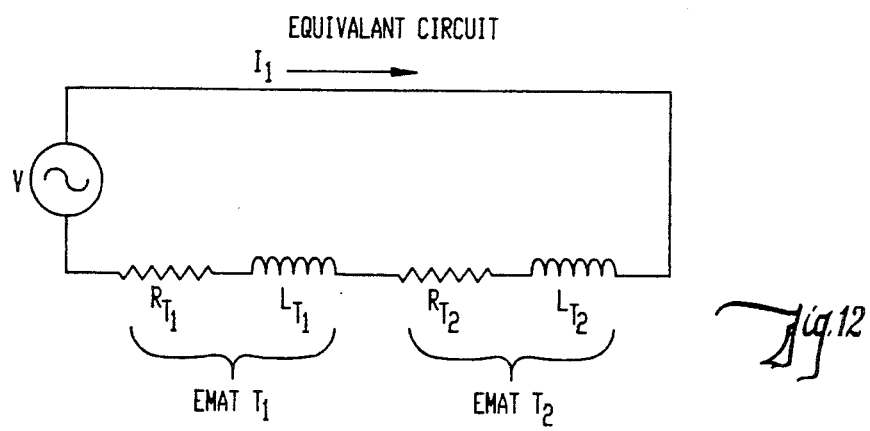
FIG. 12 is an electrical schematic of an equivalent circuit for the transducer array according to the present invention where the transmitting transducers are connected in series.

To better understand the problem and its solution, FIGS. 10–12 should be referred to. FIG. 10 shows by electrical schematic an equivalent electrical circuit for a transducer array and specimen. The transducer array, depicted to the left of FIG. 10, comprises a voltage source V, and a current $I_1$. The transducer can be represented by an inductance $L_0$ with the entire circuit also having a resistance $R_0$.

The specimen or part under analysis, such as rolled metal plate, also represents an inductance $L_1$ and a resistance $R_1$ with a hypothetical current $I_2$. A magnetic field would exist between the probe and the part based on this equivalent circuit.

FIG. 11 shows that if the probe or transducer lifts off of the part or specimen, essentially this represents a variable inductance $L_{Eq}$ and a variable resistance $R_{Eq}$. This would introduce phase shift into the circuit because of the changing relationship between the equivalent inductance and resistance.

The solution is shown in FIG. 12. The equivalent circuit whereby the transducers $T_1$ and $T_2$ are connected in series. Because each transducer would represent equivalently a resistance and inductance which is connected in series, the laws of electronics state that current $I_1$ must be the same in the entire circuit. Therefore, any phase shift regardless of lift off would be the same throughout the circuit.

It is to be understood that lift-off changes inductance as a function of distance, which in turn would change phase or shift phase for that particular transducer. If the lift off is the same for both transducers, there is no problem. It is only when there is differential lift-off (even to the 1000th of an inch) there is a problem. The driving of the transmitting transducers $T_1$ and $T_2$ in series therefore eliminates this as a problem.

Figure 13:
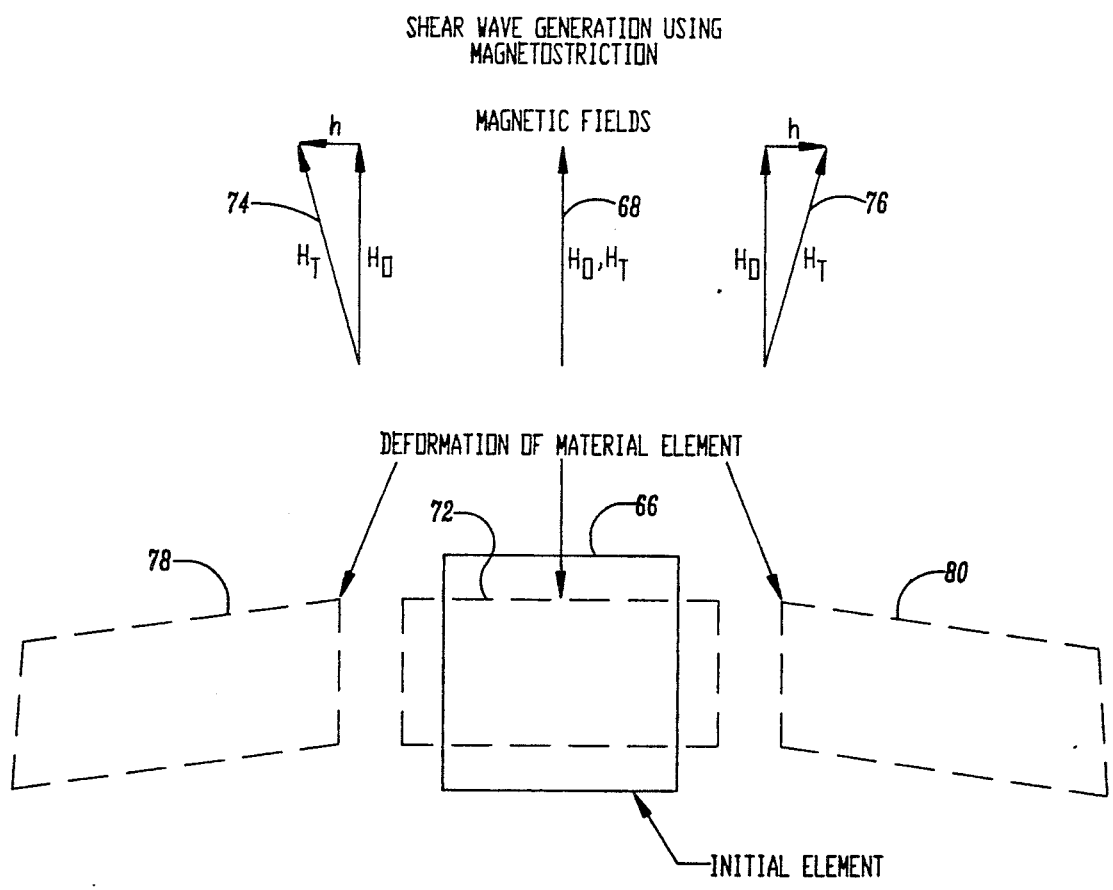
FIG. 13 is a diagrammatic representation of the generation of shear waves by magnetostriction.
Figure 14:
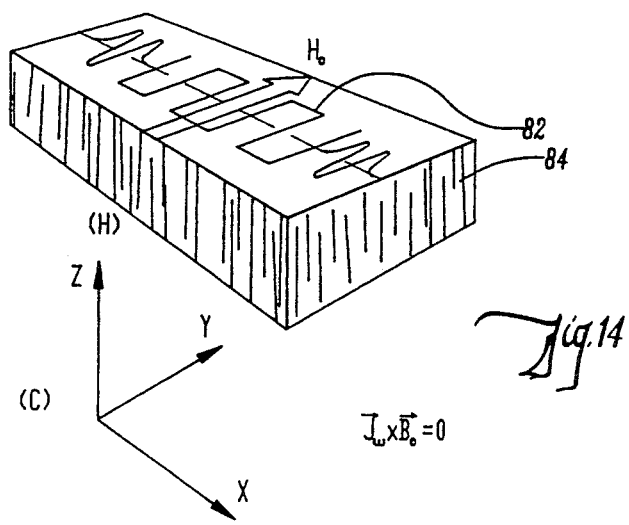
FIG. 14 is a schematic depiction of a transducer format for generating horizontally polarized shear waves according to the present invention.

FIGS. 13 and 14 depict how shear waves can be generated by magnetostriction in ferrous materials. FIG. 13 shows that a change in magnetic field in ferrous material generates forces which actually deform the material. Solid square 66 represents an initial ferrous specimen. With the application of a magnetic field depicted by vector $H_O$, $H_t$ in the directions shown by vector 68, magnetostriction forces deform specimen 66, which is exaggerated by dashed line 72. As the direction of magnetic field changes, as indicated schematically by vector 74 and 76, forces will deform specimen 66 in the manner shown by dashed lines 78 and 80 respectively. These again are exaggerated for illustration.

Such deformation, however, creates ultrasonic waves of a shear wave nature because of the back and forth deformation of the specimen 66. Therefore, as shown in FIG. 14, by placing a meander coil 82 on an element 84, an EMAT transducer for generating horizontally polarized shear waves is created. Such an EMAT can be utilized to produce shear waves for use in the present invention.

Figure 15:
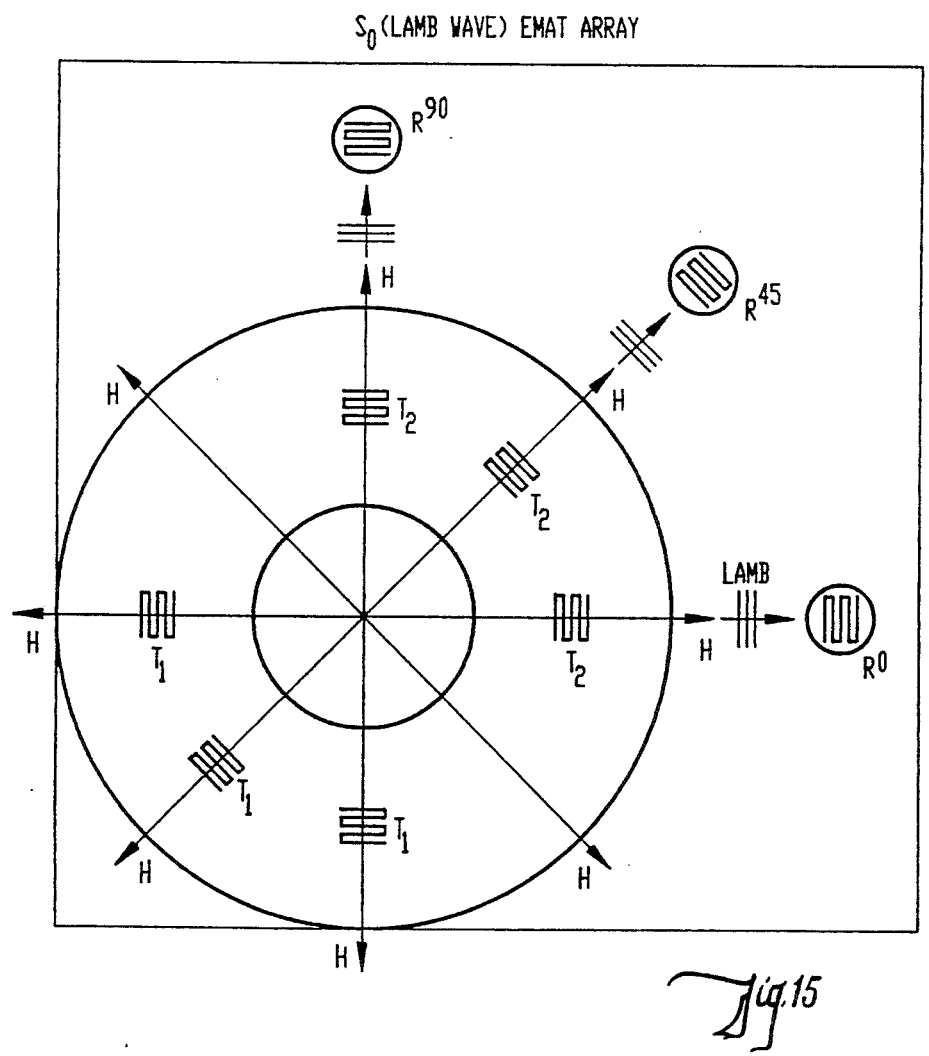
FIG. 15 is a schematic representation of a transducer array for generating Lamb or extensional ultrasonic waves according to the present invention.

FIG. 15 depicts a preferred embodiment for a transducer head 18 which could be used according to the present invention. In the configuration shown in FIG. 15, transducer head 18 would contain three arrays of transducers identified as in FIG. 4 by $T_1$, $T_2$, $R^0$; $T_1$, $T_2$, $R^{45}$; $T_1$, $T_2$, $R^{90}$ (relating to the angular orientation of the arrays with respect to 0°, 45°, and 90°). Such a configuration, as can be easily understood, would allow three arrays to be included in one transducer head 18. Additionally, it is to be understood that the transducers in FIG. 15, being positioned perpendicularly to the axis of each array, generate Lamb waves. By rotating or replacing the transducer coils so that the coils are aligned parallel with the axis of each array, shear waves could be produced.

The configuration of FIG. 15 also indicates how such a transducer head would allow precise placement of each transducer $T_1$, and $T_2$ with respect to one another for all array sets.

It can therefore be seen that the invention achieves at least all of its stated objectives. The means and method of the present invention utilize a combination of ultrasonic velocity measurement techniques utilizing EMAT transducers to derive information regarding stress and texture in plate or sheet materials. The enhancements of the invention allow a field instrument to be created which can efficiently and economically be used to nondestructively evaluate materials in process or in their environment.

It will be appreciated that the present invention can take many forms and embodiments. The true essence and spirit of this invention are defined in the appended claims, and it is not intended that the embodiments of the invention presented herein should limit the scope thereof.

For example, it is to be understood that the exact configurations of the EMAT transducers can take on different forms and embodiments. The EMATs only need to operate in the manner required to produce ultrasonic waves of the nature required for generation of particular waves in particular directions for the velocity measurements.

Furthermore, the invention can be utilized on a variety of materials. It is believed, however, to operate best with regard to plate or sheet material of less than ¼" thickness.

Still further, it is again noted that measurements at different angular orientations can be made by a single array which is rotated to the different angular orientations, or by a plurality of arrays fixed in those angular orientations to one another.

Operation of the EMATs can either be automatic or manually activated. Control apparatus can be operated automatically, semiautomatically, or allow manual operation of the entire process.

The nature of the EMATs, and the distances between the transmitting EMATs $T_1$, $T_2$ along with the distance to receiving EMATs R can be varied according to need and desire. Likewise, the choice of the bandwidth or the waves generated by the EMATs is important to the invention, but can be varied according to need and desire.

It is to be understood that generation of shear waves for nonferrous materials can be done utilizing permanent non-periodic magnets in the EMATs. However, for ferrous materials, it requires pulsed electromagnets to generate the magnetostriction. Permanent magnets are not powerful enough to accomplish this. Utilization of pulsed electromagnets is needed to saturate the element and drive out any competing magnetization.

The present invention can also be utilized to derive material properties related to stress or texture. For example, Young's modulus and R-ratios can be derived. The wave velocities are utilized to derive information which can be converted into texture and stress information.

The general frequency of operation for the EMAT driver is 450–600 KHz. Sampling period is 100 ns whereas the required time measurement accuracy needs a resolution of 0.1 ns.

What is claimed is:

1. A method for field ultrasonic measurement of texture, stress, and related material properties including but not limited to formability parameters comprising:
   positioning an array of electromagnetic acoustic transducers along an axis;
   fixing first and second of said transducers of the array at a precisely known distance from one another along the axis;
   fixing a third said transducer of the array a distance along the axis from the first and the second transducers but not between the first and second transducers; and
   driving the first and second transducers in series to produce separate ultrasonic waves which are received by the third transducer, the first and second transducers being driven in series to prevent any differences in phase between the ultrasonic waves launched by the first and second transducers caused by differential lift off of one or both of the first and second transducers.

2. The method of claim 1 wherein at least one transducer is a Lamb wave producing transducer.

3. The method of claim 1 wherein at least one transducer includes a magnet, the magnet being a pulsed electromagnet.

4. The method of claim 1 wherein a metal plate having a rolling direction is measured by orienting the array of transducers in relationship to the rolling direction of metal plate.

5. The method of claim 4 wherein the array of transducers is angularly adjustable between at least 0°, 45° and 90° with respect to the rolling direction of the plate.

6. The method of claim 1 wherein at least one transducer is a horizontally polarized shear wave producing transducer.

7. The method of claim 1 wherein at least one transducer includes a magnet, the magnet being a permanent magnet.

8. A method of performing ultrasonic measurements to analyze one or more of texture, stress, and related material properties including but not limited to formability parameters, in ferrous and non-ferrous material comprising:
   generating ultrasonic energy in the form of ultrasonic waves in the material by utilizing a first pair of electromagnetic acoustic transducers connected in series to generate said ultrasonic energy in two bursts which propagate through the material;
   receiving said bursts at a third ultrasonic electromagnetic acoustic transducer and measuring the received bursts as a function of time;
   Fourier transforming the measured, received bursts as a function of time to convert information contained in the received bursts to a frequency domain;
   inferring velocities of ultrasound from variation of phase of Fourier transforms of the received bursts with frequency; and
   deriving one or more of texture, stress, formability or related parameters by correlation with the velocities.

9. The method of claim 8 wherein the ultrasonic waves are Lamb waves generated in ferrous materials with said electromagnetic acoustic transducers each including at least one pulsed electromagnet.

10. The method of claim 8 wherein the ultrasonic waves are horizontally polarized shear waves generated in ferrous materials with said electromagnetic acoustic transducers including at least one pulsed electromagnet.

11. The method of claim 8 wherein the ultrasonic waves are Lamb waves generated in non-ferrous materials with said electromagnetic acoustic transducers including at least one permanent magnet.

12. The method of claim 8 wherein the ultrasonic waves are horizontally polarized shear waves generated in non-ferrous materials with said electromagnetic acoustic transducers including at least one permanent magnet.

13. A field instrument for ultrasonic measurement of texture, stress and related material properties including but not limited to formability comprising:
- a portable housing including control means, transducer array head connection means, first and second operation circuit means, processing means, and power supply connection means for connecting electrical power to the field instrument;
- one or more transducer array heads connectable to the transducer array head connection means;
- an array of electromagnetic acoustic transducers positioned in each transducer array head, each array including electromagnetic acoustic transducers having a means to establish a magnetic bias field;
- the first operation circuit means for firing at least two transducers of each array including firing first and second transducers of an array in series to create first and second ultrasonic bursts;
- the second operation circuit means for measuring reception of the bursts of ultrasonic energy at a third transducer of the array as a function of time;
- the processing means for processing information received at the third transducer and including means for Fourier transforming the measurements as a function of time to convert the information from a time domain to a frequency domain for inferring velocities of ultrasound from variation of phase of Fourier transforms of the information with frequency, and for deriving one or more of texture, stress, formability or related parameters by correlation with the velocities;
- the array head connection means allowing connection of a desired array of transducers for a measurement purpose; and
- the control means allowing control of the operation circuit means and processing means.

14. The field instrument of claim 13 wherein at least one electromagnetic acoustic transducer of the array includes a pulsed electromagnet.

15. The field instrument of claim 13 wherein at least one of the electromagnetic acoustic transducers of the array includes a permanent magnet.

16. A field instrument for ultrasonic nondestructive measurement of at least one of texture, stress, or related material properties including but not limited to formability, comprising:
a portable housing including:
(a) user control means for operating the instrument;
(b) processing means for data acquisition, processing of data, providing instructions for driving signals according to input from the user control means; and
(c) probe control means to provide the driving signals to a probe means for transmitting and receiving ultrasound according to instructions from the processing means;
the probe means being moveably positionable relative to the housing for placement at or near a material being measured;
a connection means operatively connecting the probe means to the housing; and
one or more arrays of electromagnetic acoustic transducers positioned in the probe means, each array consisting of at least one set of two transmitting electromagnetic acoustic transducers connected in series electrically, and at least one receiving electromagnetic transducer.

17. The instrument of claim 16 wherein at least one array includes pulsed electromagnetic acoustic transducers for generating Lamb waves to measure texture in a ferrous material.

18. The instrument of claim 16 wherein at least one array includes pulsed electromagnetic acoustic transducers for generating horizontally polarized shear weaves to measure stress in a ferrous material.

19. The instrument of claim 16 wherein at least one array includes permanent magnet electromagnetic acoustic transducers for generating Lamb waves to measure texture in a non-ferrous material.

20. The instrument of claim 16 wherein at least one array includes permanent magnet electromagnetic acoustic transducers for generating horizontally polarized shear waves to measure stress in a non-ferrous material.

21. The instrument of claim 16 further comprising two or more probe means, an array of electromagnetic acoustic transducers in each probe means being selected from the set consisting of pulsed and permanent magnet electromagnetic acoustic transducers.

22. The instrument of claim 21 wherein the electromagnetic acoustic transducers include a pulsed electromagnet to measure stress in ferrous materials.

23. The instrument of claim 21 wherein the electromagnetic acoustic transducers include a permanent magnet for measuring stress in non-ferrous materials.

24. The instrument of claim 21 wherein the electromagnetic acoustic transducers includes a pulsed electromagnet to measure texture in ferrous materials.

25. The instrument of claim 21 wherein the electromagnetic acoustic transducers includes permanent magnet for measuring texture in non-ferrous materials.

* * * * *